(12) United States Patent
Bills et al.

(10) Patent No.: US 6,436,395 B1
(45) Date of Patent: Aug. 20, 2002

(54) *ROSELLINIA SUBICULATA* ATCC 74386 AND FUNGUS ATCC 74387 FOR PRODUCING SORDARIN COMPOUNDS FOR FUNGI CONTROL

(75) Inventors: Gerald F. Bills, Clark; Anne W. Dombrowski, East Brunswick; Wendy S. Horn, Westfield, all of NJ (US); Richard K. Jansson, Doylestown, PA (US); Mark Rattray, Somerset, NJ (US); Dennis Schmatz, Cranford, NJ (US); Robert E. Schwartz, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/269,004

(22) PCT Filed: Sep. 15, 1997

(86) PCT No.: PCT/US97/16249

§ 371 (c)(1),
(2), (4) Date: Jun. 23, 1999

(87) PCT Pub. No.: WO98/11891

PCT Pub. Date: Mar. 26, 1998

Related U.S. Application Data

(60) Provisional application No. 60/026,580, filed on Sep. 18, 1996, now abandoned.

(51) Int. Cl.[7] ............... A01N 63/00; A01N 63/04; A01N 65/00; B65G 53/60; B60P 1/60
(52) U.S. Cl. ............... 424/93.5; 435/41; 435/117; 435/171; 435/254.1; 435/911
(58) Field of Search ............... 435/252.1, 254.1, 435/822, 132, 147, 155, 170, 171, 41, 117, 911; 424/93.5

(56) References Cited

U.S. PATENT DOCUMENTS

| | | | |
|---|---|---|---|
| 3,432,598 A | 3/1969 | Sigg et al. | |
| 4,483,866 A | 11/1984 | Ogata et al. | |
| 5,126,265 A | 6/1992 | Cidaria et al. | |
| 5,854,280 A | * 12/1998 | Gomez et al. | ............. 514/456 |

FOREIGN PATENT DOCUMENTS

| | | |
|---|---|---|
| GB | 1 162 027 | 8/1969 |
| WO | 96/14326 | 5/1996 |
| WO | 96/14327 | 5/1996 |

OTHER PUBLICATIONS

Bruno, "Preparation of 4–cyano–4–deformylsordaricin derivatives af fungi." Merck & Co, Inc., USA, PCT Int'l Application, US 1997–56820.*

Derwent Foreign Patent Abstract #87–090328/13 (JP 62040292).

Derwent Foreign Patent Abstract #94–221947/27 (JP 06157582).

S. J. Coval, et al., J. Antibiotics, 48:1171–1172 (1995).

D. von Hauser, et al., Helvetica Chimica Acta, 54:1178–1190 (1971).

A. C. Amadioha, Mycologia, 85:574–578 (1993).

* cited by examiner

*Primary Examiner*—David M. Naff
*Assistant Examiner*—Deborah K. Ware
(74) *Attorney, Agent, or Firm*—Shu Muk Lee; David L. Rose

(57) ABSTRACT

Disclosed is a method for controlling phytopathogenic fungi using pure strains of *Rosellinia subiculata* ATCC 74386 and fungus ATCC 74387. Further, methods of producing a sordarin compound are disclosed. The method includes cultivating each strain separately in a nutrient medium containing assimilable sources of carbon and nitrogen and recovering the compound. A sordarin compound of formula I is also disclosed. Also an antifungal composition containing a sordarin compound is also disclosed.

6 Claims, No Drawings

*ROSELLINIA SUBICULATA* ATCC 74386 AND FUNGUS ATCC 74387 FOR PRODUCING SORDARIN COMPOUNDS FOR FUNGI CONTROL

This is a 371 of PCT/US97/16249, having an international filing date of Sep. 15, 1997, which claims the benefit of U.S. Provisional Application No. 60/026,580, filed Sep. 18, 1996, now abandoned.

SUMMARY OF THE INVENTION

The present invention relates to the use of sordarin and derivatives thereof in controlling phytopathogenic fungi in crops; to agrochemical compositions containing the compounds; and to fermentation processes for the production of sordarin as well as the microorganisms used therein.

BACKGROUND OF THE INVENTION

The control of phytopathogenic fungi is of great economic importance since fungal growth on plants or on parts of plants inhibits production of foliage, fruit or seed, and the overall quality of a cultivated crop. In fact, without crop protection, greater than 75% of the world's food production would be lost. Even so, 12% is still lost to plant diseases. Because of the vast economic ramifications of fungal infection in agricultural and horticultural cultivations, a broad range of fungicidal and fungistatic products have been developed for general and specific applications. However, the widespread use of agricultural fungicides frequently induces resistance to currently available agents; thus, there exists a need to discover new antifungal compounds that are outside of the known chemical classes of agricultural fungicides, and/or act by a different mechanism than the available agents.

Sordarin (I, wherein Z is (d)) is an antifungal antibiotic isolated from the ascomycete *Sordaria araneosa* (see GB 1,162,027 and *Helvetica Chimica Acta*, 1971, 51:119–20). Other compounds having the sordarin skeleton have also been reported as antifungal agents. Japanese Kokai J62040292 discloses the compound zofimarin (I, wherein Z is (e)) isolated from *Zopfiela marina* sp.; Japanese Kokai J06157582 discloses the compound BE-31405 (I, wherein Z is (f) and $R^a$ is acetyl) isolated from Penicillium sp.; and SCH57404 (I, wherein Z is (f) and $R^a$ is methyl) is reported in *J. Antibiotics*, 1995, 48:1171–1172. Semi-synthetic sordarin derivatives are reported in PCT Applications WO96/14326 and WO96/14327. While the aforementioned compounds all have been referred to as antifungal agents, the only uses mentioned in the literature have been for treatment of human and/or animal mycotic diseases. There is no teaching or suggestion that sordarin and derivatives thereof are effective against phytopathogenic fungi, or that they are suitable for agricultural applications.

DETAILED DESCRIPTION OF THE INVENTION

The present invention provides in one aspect a method for controlling phytopathogenic fungi which comprises administering to a plant in need of such control an antifungal effective amount of a compound of formula (I)

(I)

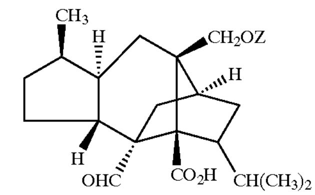

and wherein Z is a tetrahydropyrano group selected from (a)

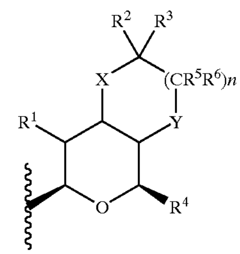

(b)

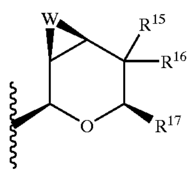

(c)

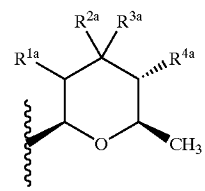

(d)

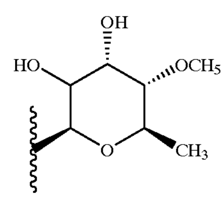

(e)

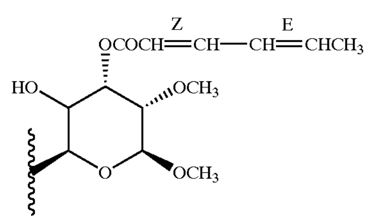

and (f)

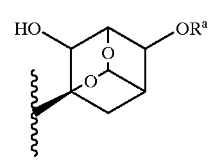

and salts and solvates (e.g. hydrates) or metabolically labile derivatives thereof, wherein $R^a$ is $OC(O)CH_3$ or $CH_3$;

$R^1$ is hydrogen, halogen, hydroxyl, $C_{1-4}$alkoxy or acyloxy;

$R^2$ and $R^3$ may each independently represent hydrogen, $C_{1-6}$alkyl or $C_{1-4}$alkoxy $C_{1-4}$alkyl, or $R^2$ and $R^3$ may together with the carbon atom to which they are attached represent C=O, C=S or $C_{3-8}$cycloalkyl;

$R^4$ is hydrogen or $CH_2R^7$ (where $R^7$ is hydrogen, hydroxyl, $C_{1-4}$alkoxy or a group $OCOR^8$ in which $R^8$ is $C_{1-4}$alkyl or aryl);

$R^5$ and $R^6$ may each independently represent hydrogen, $C_{1-6}$alkyl or $C_{1-4}$alkoxy $C_{1-4}$alkyl, or $R^5$ and $R^6$ may together with the carbon atom to which they are attached represent C=O, C=S or $C_{3-8}$cycloalkyl; n is zero or 1;

X and Y may each independently represent oxygen, sulfur or $CR^9R^{10}$ (where $R^9$ and $R^{10}$ may each independently represent hydrogen, $C_{1-6}$alkyl, $C_{1-4}$alkoxy or $C_{1-4}$alkoxyC$_{1-4}$alkyl or $R^9$ and $R^{10}$ may together with the carbon atom to which they are attached represent C=O, C=S, $C_{3-8}$cycloalkyl or C=CHR$^{11}$ where $R^{11}$ represents hydrogen or $C_{1-4}$alkyl); or when X or Y is oxygen and n is zero then —Y—CR$^2$R$^3$ or —X—CR$^2$R$^3$— respectively may also represent —N=CR$^3$— or —NR$^{12}$—CR$^2$R$^3$—(where CR$^2$ and R$^3$ are C=O and R$^{12}$ is $C_{1-4}$alkyl an acyl group COR$^{13}$ where $R^{13}$ is $C_{1-6}$alkyl) or when Y is oxygen and n is zero X may be represent the group CR$^{11}$ (wherein R$^{11}$ has the meanings defined above) which is attached to the pyran ring by a double bond;

$R^{15}$ is hydrogen, halogen, azido, $C_{1-6}$alkyl, hydroxy, $C_{1-6}$alkoxy (optionally substituted by 1 or 2 hydroxy or a ketal thereof or 1 or 2 $C_{1-3}$alkoxy groups), arylC$_{1-4}$alkoxy, $C_{3-6}$alkenyloxy, a group OCOR$^{18}$ (where $R^{18}$ is arylC$_{1-4}$alkoxy or a $C_{1-10}$alkyl group optionally containing one or two double bonds) or $C_{1-6}$alkoxycarbonyl $C_{1-4}$alkoxy, and $R^{16}$ represents hydrogen or $R^{15}$ and $R^{16}$ may together with the carbon atom to which they are attached represent C=O or C=CH$_2$;

$R^{17}$ is CH$_2$R$^{19}$ where $R^{19}$ is hydrogen, hydroxyl, $C_{1-4}$alkoxy or a group OCOR$^{20}$ in which $R^{20}$ is $C_{1-4}$alkyl); and W is oxygen, sulfur, or CH$_2$; and the dotted line in group (a) indicates the optional presence of an additional bond;

$R^{1a}$ is hydrogen, halogen, hydroxyl or $C_{1-4}$alkoxy;

$R^{2a}$ hydrogen, halogen, hydroxyl, $C_{1-10}$alkoxy, $C_{1-10}$alkylthio, $C_{1-6}$alkoxyC$_{1-4}$alkoxy, arylC$_{1-6}$alkyloxy, arylC$_{3-6}$alkenyloxy, azido, NR$^{5a}$ COR$^{5a}$ (where each $R^{5a}$ is independently hydrogen or $C_{1-6}$alkyl), OR$^{6a}$ (where $R^{6a}$ is a cyclic ether containing 4 to 8 atoms linked to the oxygen atom via a ring carbon atom adjacent to the ring oxygen atom) or a group Y$^a$C(=O) —X$^a$—R$^{7a}$ where Y$^a$ is oxygen, sulfur or NH, X$^a$ is either a bond, an oxygen atom or a moiety NR$^{8a}$ in which R$^{8a}$ is hydrogen or $C_{1-6}$alkyl, and $R^{7a}$ is $C_{1-10}$alkyl optionally containing one or two double bonds, aryl, arylC$_{1-4}$alkyl, arylC$_{2-4}$alkenyl, haloC$_{1-6}$alkyl, or $C_{1-6}$alkoxyC$_{1-4}$alkyl), and $R^{3a}$ represents hydrogen, or $R^{2a}$ and $R^{3a}$ may together with the carbon atom to which they are attached represent C=O or C=NOR$^{9a}$ (where $R^{9a}$ is $C_{1-6}$alkyl); and $R^{4a}$ is hydroxyl, $C_{1-6}$alkoxy or OC(=O)R$^{7a}$ (where $R^{7a}$ is as defined above); with the proviso that when $R^{1a}$ represents a hydroxyl group in the axial configuration and $R^{4a}$ is methoxy then $R^{2a}$ cannot represent a group in the axial configuration selected from hydroxyl and OCOCHCH$^Z$=CH—CH$^E$=CHCH$_3$.

In another aspect the present invention provides an agricultural composition for use in controlling phytopathogenic fungi which comprises an antifungal effective amount of a compound of formula I and an agriculturally acceptable carrier.

Another aspect of the present invention provides a process for the production of sordarin which comprises:

cultivating a sordarin producing strain of *Rosellinia subiculata* in a nutrient medium containing assimilable sources of carbon and nitrogen; and isolating sordarin.

Another aspect of the present invention provides a biologically pure culture of *Rosellinia subiculata* having the identifying characteristics of ATCC 74386.

A further aspect of the present invention provides a process for the production of sordarin which comprises:

cultivating a sordarin producing strain of a fungus having the identifying characteristics of ATCC 74387 in a nutrient medium containing assimilable sources of carbon and nitrogen; and isolating sordarin.

Another aspect of the present invention provides a biologically pure culture of a fungus having the identifying characteristics of ATCC 74387.

In the application, unless otherwise specified, the following definitions apply:

The term "control" or "controlling" includes prophylactic use (i.e. to protect against infection) and curative use (i.e. to eradicate infection).

The term "plants" include whole live plants or parts thereof, foliage, flowers, seeds, fruits, and other materials derived from plants. The term also includes roots of the plant via application of the active ingredient to the soil.

The term "composition", as in agricultural or agrochemical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the compositions of the present invention encompass any composition made by admixing a compound of the present invention and an agriculturally acceptable carrier.

"Alkyl" as a group or part of a group means a straight or branched chain alkyl moiety such as methyl, ethyl, n-propyl, n-butyl, isopropyl, s-butyl, t-butyl, n-hexyl and n-octyl.

"Aryl" as a group or part of a group means phenyl or heteroaryl each optionally substituted by one to three groups independently selected from halogen, hydroxyl, $C_{1-6}$alkyl, $C_{1-6}$alkoxy or $C_{1-4}$alkoxycarbonyl. The heteroaryl group may be a 5- or 6-membered heteroaromatic ring containing one or more heteroatoms selected from nitrogen, oxygen and sulfur. Suitable examples of heteroaryl groups include pyridyl, furyl, thienyl and pyrrolyl.

"Halogen" or "halo" means fluorine, chlorine, bromine or iodine.

When $R^1$ is an acyloxy group it may represent, for example a group OCOR$^{13}$ where $R^{13}$ is as defined above.

Suitable salts of a compound of formula I include inorganic base salts such as alkali metal salt (e.g. sodium and potassium salts), ammonium salts, and organic base salts. Suitable organic base salts include amine salts such as trialkylamine (e.g. triethylamine), dialkylamine salts (e.g. dicyclohexylamine), optionally substituted benzylamine (e.g. phenylbenzylamine or p-bromobenzylamine), ethanolamine, diethanolamine, N-methylglucosamine, N-methylpiperidine, pyridine and substituted pyridine (e.g. collidine, lutidine, 4-dimethylaminopyridine), and tri (hydroxymethyl)methylamine salts, and amino acid salts (e.g. lysine or arginine salts).

Metabolically labile derivatives of compounds of formula I are compounds which are converted in the subject being treated (be it the plant, foliage, flower, fruit, seed, or other parts or product of the plant, or the soil) into compounds of formula I. Examples of such derivatives include conventional metabolically labile esters formed from the carboxylic acid in the molecule.

In one preferred embodiment the compound of formula I is sordarin.

In another preferred embodiment, the phytopathogenic fungi being controlled are Erysiphe spp. (powdery mildew) and other powdery mildews such as, Sphaerotheca spp, Podosphaera spp., an[0084] Uncinula spp.; Puccinia spp. (rusts); Rhizoctonia spp; Ustilago spp. (smut); Venturia spp. (scab) Helminthosporium spp. (Curvularia, Drechslera, Exserohilum spp.); Stagnospora spp.; Septoria spp.; Botrytis spp. (gray mold); Cercospora spp.; Pseudocercosporella spp.; Pyricularia spp.; Phytophthora spp.; Fusarium spp; Verticillium spp.; Plasmopara spp.; Alternaria spp.

The more preferred embodiment of these phytopathogenic fungi being controlled are *Erysiphe graminis, Puccinia recondita, Stagnospora nodorum, Septoria tritici, Pyricularia oryzae, Phytophthora infestans, Plasmopara viticola* and *Botrytis cinerea*.

In another embodiment, the plants treated are: cereal crops (e.g. wheat, rye, oat, barley, rice, sorghum and related crops); beet (sugar beet and fodder beet); pomes, dropes and soft fruit (e.g. apples, pears, plums, peaches, almonds, cherries, strawberries, raspberries, and blackberries); leguminous plants (e.g. beans, peas, lentils and soybeans); oil plants (rape, mustard, poppy, olives, sunflowers, coconut, castor oil plants, cocoa beans and groundnuts); curcubits (e.g. cucumber, squash, and melon); fiber plants (e.g. cotton, flax, hemp, and jute); citrus fruit (e.g. oranges, lemons, mandarins and grapefruit); vegetables (e.g. lettuce, cabbage, spinach, carrot, asparagus, paprika, onions, tomatoes, and potatoes); Lauraceae: (avocados, cinnamon and camphor); or plants such as maize, tobacco, nuts, coffee, sugar cane, tea, vines, hops, bananas and natural rubber plants, as well as ornamentals (flowers, shrubs, broad-leaved trees and evergreens, such as conifers).

Preparation of Compounds. Compounds of formula I are all known compounds and methods for their preparation are available in the literature.

Sordarin (I, wherein Z is (d)) can be obtained by the cultivation of *Sordaria araneosa* NRRL 3196 (also deposited with the ATCC as ATCC 36386) according to the procedure described in GB1,162,027 or in WO96/14326. Sordarin can also be isolated from the fermentation of *Rosellinia subiculata* and an unidentified fungus ATCC 74387 as described hereinbelow.

Zofirmarin (I, wherein Z is (e)) may be obtained from the fermentation broth of *Zofiela marina* SANK 21274 (ATCC 34456) as described in Japanese Kokai 62040292. BE31405 (I, wherein A is (f) and $R^a$ is acetyl) is produced by Penicillum sp. F31405 as described in Japanese Kokai 06157582. SCH57404 (I, wherein A is (f) and $R^a$ is methyl) is produced by a fungus identified as Schering culture number SCF1082A as reported in *J. Antibiotics*, 1995, 48(10):1171–1172.

Sordarin derivatives (I, wherein Z is (a) or (b)), and their preparation are described in PCT Application WO96/14326; and sordarin derivatives (I, wherein Z is (c)) and their preparation are described in PCT Application WO96/14327.

As mentioned above, two other organisms have been found to produce sordarin.

One of the fungal strains used to produce sordarin is an unidentified sterile fungus GB3109 that was isolated from the internal tissues of roots of a mangrove shrub, *Conocarpus erectus* (Combretaceae), collected in the Manglar de Río Rincón, Península de Osa, Provincia de Puntarenas, Costa Rica, and identified as MF6232 in the culture collection of Merck & Co., Inc., Rahway, N.J. This culture was deposited on Aug. 27, 1996 in the permanent collection at the American Type Culture Collection, 12301 Parklawn Drive, Rockville, Md. 20852, USA under the terms of The Budapest Treaty on the International Recognition of the Deposit of Microorganisms for the Purposes of Patent Procedure, and assigned the accession number ATCC 74387.

The fungus was grown on a variety of mycological media, under different light regimes, and on sterilized leaves and filter paper but in all cases, it has failed to produce reproductive structures and thus cannot be identified.

In agar culture, colonies of the fungus exhibit the following morphology:

Colonies on oatmeal agar (Difco) at 23° C., 12 hr photoperiod, growing moderately fast, attaining 85–90 mm in 14 days, with advancing zone appressed, even, obscurely zonate, strongly radially striate, with moist appressed mycelium at the center, becoming silky with radiating prostrate hyphal bundles or strands, translucent to pale pink, near Pale Ochraceous Salmon (capitalized color names from Ridgway, R. 1912. Color Standards and Nomenclature, Washington, D.C.), Light Ochraceous Salmon, pinkish gray Avellaneous, Cinnamon-Drab, or white in uppermost aerial mycelium, reverse pale pinkish gray, exudates absent, odor faintly fragrant. No growth at 37 C on oatmeal agar.

Colonies on V8 juice agar (Stevens, R. B. 1981. Mycology Guidebook. University of Washington Press, Seattle, pg. 665) at 23° C., 12 hr photoperiod, growing slowly attaining 37–42 mm in 14 days, submerged to at the margin, mostly with appressed most mycelium, with some scant floccose aerial mycelium towards outer third, zonate, translucent to pale grayish pink, similar to color on oatmeal agar, reverse translucent to pale reddish brown, near Wood Brown, Fawn Color.

Colonies on cornmeal agar (Difco) at 25° C., 12 hr photoperiod, growing slowly, attaining 33–34 mm in 14 days, with margin submerged, lacking aerial hyphae, zonate, translucent.

The mycelium is composed of highly branched, simple septate, hyaline hyphae.

The second fungal strain (GB3719) used to produce sordarin is a strain of *Rosellina subiculata* (Ascomycotina, Xylariaceae), designated as MF6239 in the culture collection of Merck & Co., Inc., Rahway, N.J. This culture was deposited on Aug. 27, 1996 in the permanent collection at the American Type Culture Collection, 12301 Parklawn Drive, Rockville, Md. 20852, USA under the terms of The Budapest Treaty on the International Recognition of the Deposit of Microorganisms for the Purposes of Patent Procedure, and assigned the accession number ATCC 74386.

Ascomata of *Rosellinia subiculata* (GB3719) were found on a decorticated hardwood limb on the shore of the Navesink River, Monmouth Co., N.J. In the laboratory, the apices of several ascomata were removed with a sterilized microtome blade and asci, paraphyses and ascospores from the centrum were removed with an insect pin and streaked onto malt-yeast extract agar. Ascospores were incubated overnight until they germinated and were transferred to tubes of malt-yeast extract agar to initiate pure colonies.

The morphology of *Rosellinia subiculata* (GB3719) generally conformed to descriptions in the literature (J. B. Ellis & B. M. Everhart. 1892. The North American Pyrenomycetes. Published by the authors, Newfield, N.J. pg. 165–166; L. E. Petrini. 1993. Rosellinia species of the temperate zones. Sydowia 44:169–281). The key features that lead to identification of the fungus as *Rosellinia subiculata* were: stromatic ascomata occurring singly but aggregated or fused in small clusters on a mycelial subiculum on decorticated wood; stromata were hemispherical, papillate, smooth, shiny, black, subiculum a thin mycelial mat, pale buff, or sometimes appearing only as a lightly colored discoloration of the wood adjacent to the stromata; asci were cylindrical with an amyloid apical plug; ascospores were brownish gray, broadly elliptical to slightly reniform, smooth, without appendages or sheaths, with a straight, ventral germ slit, 10–12×5–6 μm.

In agar culture, colonies of the fungus exhibit the following morphology:

Colonies on oatmeal agar at 23° C., 12 hr photoperiod, growing moderately fast, attaining 73–75 mm in 14 days, with advancing zone appressed, even, obscurely zonate, with white velvety to floccose mycelium over inner third, with moist appressed mycelium over outer two-thirds, translucent to white or pale pink, pale vinaceous pink, Light Vinaceous Cinnamon in reverse, exudates absent, slightly fragrant odor. No growth at 37 C on oatmeal agar.

Colonies on V8 juice agar at 23° C., 12 hr photoperiod, growing slowly attaining 25–35 mm in 14 days, submerged at the margin, mostly with appressed most mycelium, with some floccose aerial mycelium towards inner third, zonate, translucent to pale grayish pink, Vinaceous Cinnamon, reverse translucent to cinnamon, Orange-Cinnamon, Cinnamon, or pale reddish brown, Russet, Fawn Color, odor fragrant.

Colonies on cornmeal agar at 25° C., 12 hr photoperiod, growing slowly, attaining 29–34 mm in 14 days, with margin submerged, lacking aerial hyphae, azonate, translucent, or with scant white mycelium at inoculation point, colorless in reverse.

When first grown in culture in August of 1993, the strain produced scant conidiophores and conidia of a Geniculosporium anamorph similar to that described by Petrini 1993. However, sporulation is no longer apparent, most likely due to prolonged storage and repeated transfers. At least in one case, a few mature perithecia with asci and ascospores identical to those observed in nature were formed after 5 weeks growth on oatmeal agar. Ascospores germinated overnight when incubated on malt-yeast extract agar at room temperature. The mycelium is composed of highly branched, simple septate, hyaline hyphae.

Sordarin is produced by cultivating a strain of *Rosellina subiculata* or the unidentified fungus MF6232 (ATCC74387) capable of producing said compound on a conventional solid medium or in a conventional aqueous medium. The organism is grown in a nutrient medium containing known nutritional sources for similar fungi, i.e. assimilable sources of carbon and nitrogen plus optional inorganic salts and other known growth factors. The general procedures used for the cultivation of other similar fungi are applicable to the present invention.

The nutrient medium should contain an appropriate assimilable carbon source such as ribose, glucose, sucrose, cellobiose or fructose. As nitrogen source, ammonium chloride, ammonium sulfate, urea, ammonium nitrate, sodium nitrate, etc. may be used either alone or in combination with organic nitrogen sources such as peptone, fish meal extract, yeast extract, corn steep liquor, soybean powder, cotton seed flour, etc. There may also be added, if necessary, nutrient inorganic salts to provide sources of sodium, potassium, calcium, ammonium, phosphate, sulfate, chloride, bromide, carbonate, zinc, magnesium, manganese, cobalt, iron, and the like.

Production of sordarin may be effected at any temperature conducive to satisfactory growth of the producing organism, e.g. 30° C. Ordinarily, optimum production of the desired compound is obtained in shake flasks after incubation periods of 7–21 days. Aeration in shake flasks is achieved by agitation, e.g. shaking on a rotary shaker. If fermentation is to be carried out in tank fermentors, it is desirable to produce a vegetative inoculum in a nutrient broth by inoculating the broth culture from slant culture, lyophilized culture or frozen culture of the organism. After obtaining an active inoculum in this manner, it is aseptically transferred to the fermentation tank medium. Production of the desired compound in tank fermentors usually reaches the optimum after 7 to 21 days of incubation. Agitation in the tank fermentor is provided by stirring and aeration may be achieved by injection of air or oxygen into the agitated mixture. Compound production may be monitored using chromatographic or spectroscopic techniques, or by a conventional biological assay.

In a preferred embodiment, the producing strain is *Rosellina subiculata* having the identifying characteristics of ATCC 74386, or a mutant or a variant thereof.

In another preferred embodiment, the producing strain of the unidentified fungus is ATCC 74387.

Sordarin is readily recovered from fermentation broth by extracting the whole broth with an organic solvent such as methyl ethyl ketone. The compounds may be purified using standard methods well known in the art such as gel filtration chromatography, thin layer chromatography, high performance liquid chromatography, concentration, precipitation and/or crystallization, or combinations thereof. Alternatively, the whole broth or an organic extract thereof may be spray-dried or freeze-dried, followed by purification as above mentioned.

Utility. Compounds of formula I have use as broad spectrum crop antifungal agents and are extremely effective on a broad spectrum of phytopathogenic fungi, in particular those from the following classes (consisting of): Deuteromycetes (e.g. Botrytis spp., Septoria spp., Pyricularia spp., Stagnospora spp., Helminthosporium spp. (Curvularia, Drechslera, Exserohilum spp.), Fusarium spp., Cercospora spp., Rhynchosporium, spp. Pseudocercosporella, spp. and Alternaria spp.); Basidiomycetes (e.g. Puccinia spp., Rhizoctonia spp., and Hemileia); Ascomycetes (e.g. Venturia spp., Podospharera spp., Erysiphe spp., Monilinia spp. and Uncinula spp.); and Oomycetes (e.g. Phytophthora spp., Pernospora spp., Bremia spp., Pythium spp., and Plasmopara spp.). The foregoing list exemplifies the phytopathogenic fungi against which the named compounds demonstrate activity, and is not limiting in any manner. These compounds have very advantageous curative, preventive and systemic fungicidal properties for protecting plants, and can be used to inhibit or to destroy the microorganisms occurring on plants or on parts of plants (the fruit, blossom, leaves, stalks, tubers or roots) of different crops of useful plants, while at the same time parts of plants that grow later are also protected against such microorganisms. They can also be used as dressings in the treatment of plant propagation material, especially seed (fruit, tubers, grain) and plant cuttings (for example rice), to provide protection against fungal infections and against phytopathogenic fungi occurring in the soil. Compounds of formula I of the invention are distinguished by the fact that they are especially well tolerated by plants and are environmentally friendly.

Based on the spectrum of activity, the compounds of the present invention can be used to protect or cure plants of phytopathogenic fungi affecting various useful crops. The following species of plants are suitable for the use described in the scope of the invention of the stated compounds: cereal (e.g. wheat, rye, oat, barley, rice, sorghum and related crops); beet (sugar beet and fodder beet); pomes, dropes and soft fruit (e.g. apples, pears, plums, peaches, almonds, cherries, strawberries, raspberries, and blackberries); leguminous plants (e.g. beans, peas, lentils and soybeans); oil plants (rape, mustard, poppy, olives, sunflowers, coconut, castor oil plants, cocoa beans and groundnuts); curcubits (e.g. cucumber, squash, and melon); fiber plants (e.g. cotton, flax, hemp, and jute); citrus fruit (e.g. oranges, lemons, mandarins and grapefruit); vegetables (e.g. lettuce, cabbage, spinach, carrot, asparagus, paprika, onions, tomatoes, and potatoes); Lauraceae: (avocados, cinnamon and camphor); or plants such as maize, tobacco, nuts, coffee, sugar cane, tea, vines, hops, bananas and natural rubber plants, as well as ornamentals (flowers, shrubs, broad-leaved trees and evergreens, such as conifers). However, the aforementioned plant species do not constitute a limiting list of plants with respect to spectrum by the stated compounds.

The compounds of formula I are particularly useful for controlling the following plant diseases:

*Erysiphe graminis* (powdery mildew) on wheat, barley, oat, rye and turf and other powdery mildews on various hosts such as, *Erysiphe cichoracearum* and *Sphaerotheca fuliginea* on cucurbits, *Podosphaera leucotricha* on apples, *Uncinula necator* on vines; Puccinia species (rusts) on wheat, barley and other hosts; *Rhizoctonia solani* in cotton, Ustilago species (smut) in cereals and sugar cane, *Venturia inaequalis* (scab) in apples, Helminthosporium (Curvularia, Drechslera, Exserohilum) species in cereals, *Stagnospora nodorum* and *Septoria tritici* in wheat, *Botrytis cinerea* (gray mold) in strawberries and grapes, *Cercospora arachidicola* in groundnuts, *Pseudocercosporella herpotrichoides* in wheat and barley, *Pyricularia oryzae* in rice, *Phytophthora infestans* in potatoes and tomatoes, Fusarium and Verticillium species in various plants, *Plasmopara viticola* in grapes, Alternaria species in fruit and vegetables. The compounds of formula I may also be used for protecting materials (e.g. preservation of timber against Paecilomyces variotii).

Agrochemical Compositions. The compounds of formula I can be used in either an unmodified form or preferably together with adjuvants conventionally employed in the art of agrochemical formulation and are for this purpose forms known mainly as: emulsifiable concentrates, coatable pastes, directly sprayable or dilutable solutions, dilute solution, suspensions (including high-percentage aqueous, oily or other suspensions), dispersions, oil dispersions, broadcasting agents, wettable powders, soluble powders, dusts, granules, and encapsulations. The formulations are prepared in known manner, e.g. by homogeneously mixing and/or grinding the active ingredients with extenders, e.g. solvents, solid carriers and, where appropriate, surface-active compounds (surfactants). Powders, dusts and broadcasting agents may be prepared by mixing or grinding the active ingredients with a solid carrier. Granules, e.g., coated, impregnated or homogeneous granules, may be prepared by bonding the active ingredients to solid carriers.

Suitable solvents are: aromatic hydrocarbons, preferably the fractions containing 8 to 12 carbon atoms, such as xylene mixtures or substituted naphthalenes, chlorinated aromatics such as chlorobenzenes, phthalates, such as dibutyl or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones such as cyclohexanone, amines such as ethanolamine, strongly polar solvents, such as N-methyl-2-pyrrolidone, dimethyl sulfoxide or dimethylformamide, and vegetable oils or epoxidised vegetable oils, such as epoxidised coconut oil or soybean oil; and water.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Examples of solid carriers are mineral earths such as silicic acids, silica gels, silicates, talc, kaolin, attapulgus clay, limestone, lime, chalk, bole, loess, clay, dolomite, diatomaceous earth, aluminas calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

Compounds of formula I may be mixed and applied together with other active ingredients, for example herbicides, insecticides, bactericides, nematocides, molluscicides, growth regulators, micronutrients, and fertilizers. The other ingredients may also be one or more fungicides belonging to but not restricted to the following classes of fungicides: carboxamides, benzimidazoles, triazoles, hydroxypyridines, dicarboxamides, phenylamides, thiadiazoles. carbamates, cyano-oximes, cinnamic acid derivatives, morpholines, imidazoles, β-methoxy acrylates and pyridines/pyrimidines. Furthermore, these additional active ingredients may be used as mixtures of several of the preparations, if desired together with other application promoting adjuvants usually used in the art of formulation. Suitable carriers and adjuvants can be solid or liquid and correspond to the substances typically used in formulation technology (e.g. natural or regenerated mineral substances, solvents, disperants, and wetting agents).

The following list of fungicides with which compounds of formula I may be combined is intended to illustrate possible combinations but not to impose any restrictions. Examples of fungicides which may be combined with compounds of formula I are: sulfur, dithiocarbamates and their derivatives, such as ferric dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfides, ammonia complex of zinc N,N'-ethylenebisdithiocarbamate, ammonia complex of zinc N,N'-propylenebisdithiocarbamate, zinc N,N'-propylenebisdithiocarbamate and N,N'-polypropylenebis(thiocarbamyl) disulfide; nitro derivative, such as dinitro(1-methylheptyl)-phenyl crotonate, 2-sec-butyl-4,6-dinitrophenyl 3,3-dimethylacrylate,2-sec-butyl-4,6-dinitrophenyl isopropylcarbonate and diisopropyl 5-nitroisophthalate; heterocyclic substances, such as 2-heptadecylimidazol-2-yl acetate, 2,4-dichloro-6-(o-chloroanilino)-s-triazine, O,O-diethyl phthalimidophosphonothioate, 5-amino-1-[bis-(dimethylamino)-phosphinyl]-3-phenyl-1,2,4-triazole, 2,3-dicyano-1,4-dithioanthraquinone, 2-thio-1,3-dithio[4,5-b]quinoxaline, methyl 1-(butylcarbamyl)-2-benzimidazolecarbamate, 2-methoxycarbonylaminobenzimidazole, 2-(fur-2-yl)-benzimidazole, 2-(thiazol-4-yl)benzimidazole, N-(1,1,2,2-tetrachloroethylthio)-tetrahydrophthalimide, N-trichloromethylthiotetrahydrophthalimide, N-trichloromethylthiophthalimide, N-dichlorofluoromethylthio-N',N'-dimethyl-N-phenylsulfuric acid diamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, 2-thiopyridine 1-oxide, 8-hydroxyquinoline and its copper salt, 2,3-dihydro-5-carboxanilido-6-methyl-1,4-oxathiyne, 2,3-dihydro-5-carboxanilido- 6-methyl-1,4-oxathiyne 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, 2,5-dimethyl-N-cyclohexylfuran-3-carboxamide, N-cyclohexyl-N-methoxy-2,5-diethylfuran-3-carboxamide, 2-methylbenzanilide, 2-iodobenzanilide, N-formyl-N-morpholine-2,2,2-trichloroethylacetal, piperazine-1,4-diylbis-(1-(2,2,2-trichloroethyl)-formamide), 1-(3,4-dichloroanilino)-1-formylamino-2,2,2-trichloroethane, 2,6-dimethyl-N-tridecylmorpholine and its salts, 2,6-dimethyl-N-cyclododecylmorpholine and its salts, N[3-(p-tert.-butylphenyl)-2-methylpropyl]-cis-2,6-dimethylmorpholine, N-3-(p-tert.-butylphenyl)-2-methylpropyl]-piperidine, 1-2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N]-imidazolylurea, 1-(4-chlorophenoxy)-3,3-dimethyl-1-(1H-1,2,4-triazol-1-yl)-butan-2-one, 1-(4-chlorophenoxy)-3,3-dimethyl-1-(1H-1,2,4-triazol-1-yl)-butan-2-ol, alpha-(2-chlorophenyl)-alpha-(4-chlorophenyl)-5-pyrimidinemethanol, 5-butyl-(2-dimethylamino-4-hydroxy-6-methylpyrimidine, bis-(p-chlorophenyl)-3-pyridinemethanol, 1,2-bis-(3-ethoxycarbonyl-2-thioureido)-benzene, 1,2-bis-(3-methoxycarbonyl-2-thioureido)-benzene, and various fungicides, such as dodecylguanidine acetate, 3-[3-(3,5-dimethyl-2-oxycyclohexyl)-2-hydroxyethyl]-glutaramide, hexachlorobenzene, DL-methyl-N-(2,6-dimethylphehyl)-N-fur-2-yl alanate, methyl DL-N-(2,6-dimethylphenyl)-N-[2]-methoxyacetyl)-alanate, N-(2,6-dimethylphenyl)-N-chloroacetyl-DL-2-aminobutyrolactone, methyl DL-N-(2,6-dimethylphenyl)-N-(phenylacetyl)-alanate, 5-methyl-5-vinyl-3-(3,5-dichlorophenyl)-2,4-dioxo-1,3-oxazolidine, 3-[3,5-dichlorophenyl]-5-methyl-5-methoxymethyl-1,3-oxazolidine-2,4-dione, 3-(3,5-dichlorophenyl)-1-isopropylcarbamylhydantoin, N-(3,5-dichlorophenyl)-1,2-dimethylcyclopropane-1,2-dicarboximide, 2-cyano-[N-(ethylaminocarbonyl)-2-methoximino]-acetamide, 1-[2-(2,4-dichlorophenyl)-pentyl]-1H-1,2,4-triazole, 2,4-difluoro-a-(1H-1,2,4-triazol-1-ylmethyl)-benzhydryl alcohol, N-(3-chloro-2,6-dinitro-4-trifluoromethylphenyl)-5-trifluoromethyl-3-chloro-2-aminopyridine, and 1-((bis-(4-fluorophenyl)-methylsilyl)-methyl)-1H-1,2,4-triazole.

Method of Use. As with the nature of compositions, the method of application such as spraying, atomizing, dusting, scattering, coating, dressing, and pouring are chosen in accordance with the intended objectives of the application and the prevailing circumstances. One method of applying the active ingredient or agrochemical composition containing at least one of the stated compounds is application to the plants (i.e. foliar application). However, the active ingredient can also penetrate the plant through the roots via the soil (i.e. soil application). This may be in the form of either a liquid application to the soil (drench) or a granular application.

The active ingredient can also be applied to plant propagation material such as seeds (fruits, tubers or grains) or plant cuttings, in either liquid form (coating) or in solid form (dressing). Seeds, for example, can be dressed before sowing. The compounds of the invention can also be applied to grains either by impregnating the grains with a liquid formulation of by coating them with a solid formulation. The composition can also be applied to the locus of planting when planting the propagation material, for example to the seed furrow during sowing.

Advantageous rates of application are normally from 50 g to 50 kg of active ingredient (a.i.) per hectare, preferably 100 g to 2 kg a.i./ha, most preferably 100 g to 600 g a.i./ha. The active ingredients of the stated compounds are typically used in the form of compositions and can be applied to the plant, or to parts of the plant either simultaneously or in succession with further active ingredients. These further active ingredients can be fertilizers, additional micronutrients, or other plant growth affecting compounds. They can, however, also be selective herbicides, insecticides, bactericides, nematocides, insecticides, and molluscicides,as well as other fungicides.

The following examples are intended to illustrate the invention and do not limit its scope in any manner. The preparation and composition of the various seed and production media referred to in the Examples are as follows:

| SEED MEDIUM 1 | |
|---|---|
| Component | g/L |
| Yeast extract | 4.0 |
| Malt extract | 8.0 |
| Glucose | 4.0 |
| Junlon | 1.5 |

The medium was prepared with distilled water, the pH adjusted to 7.0 prior to sterilization, and was dispensed at 50 ml/ 250 ml unbaffled Erlenmeyer flask. Cotton closures were used. Sterilization was at 121° C. for 20 minutes.

SEED MEDIUM 2

| Component | (g/l) | Trace elements solution | |
|---|---|---|---|
| | | Component | (g/l) |
| Corn steep liquor (dried) | 2.5 | FeSO$_4$.7H$_2$O | 1.0 |
| Tomato paste | 40.0 | MnSO$_4$.4H$_2$O | 1.0 |
| Oat flour | 10.0 | CuCl$_2$.2H$_2$O | 0.025 |
| Glucose | 10.0 | CaCl$_2$.H$_2$O | 0.1 |
| Trace elements solution | 10.0 ml/L | H$_3$BO$_3$ | 0.056 |
| | | (NH$_4$)$_6$MoO$_{24}$.4H$_2$O | 0.019 |
| | | ZnSO$_4$.7H$_2$O | 0.2 |
| | | Trace elememts prepared in 0.6 N HCl | |

The medium was prepared with distilled water, the pH adjusted to 6.8 prior to sterilization, and was dispensed at 50 ml/ 250 ml unbaffled Erlenmeyer flask. Cotton closures were used. Sterilization was at 121° C. for 20 minutes.

Solid Production Medium 1
1. Solid portion:
   Add 675 cc vermiculite to a 2-liter roller bottle. Plug with latex closure; autoclave for 60 min., plus 30 min. dry.
2. Liquid portion:
   To a 500 ml bottle, add 220 ml of the following:

| Component | g/L |
|---|---|
| Glucose | 150.0 |
| Glycerol | 20.0 |
| Yeast extract | 4.0 |
| NaNO$_3$ | 1.0 |
| Monosodium Glutamate | 3.0 |
| Na$_2$HPO$_4$ | 0.5 |
| MgSO$_4$.7H$_2$O | 1.0 |
| K-elements | 1.0 ml/L |
| CaCO$_3$ | 8.0 |
| K-elements Component | |
| FeCl$_3$.6H$_2$O | 5.8 |
| MnSO$_4$.H$_2$O | 0.1 |
| CoCl$_2$.6H$_2$O | 0.02 |
| CuSO$_4$.5H$_2$O | 0.015 |
| Na$_2$MoO$_4$.2H$_2$O | 0.012 |
| ZnCl$_2$ | 0.02 |
| SnCl$_2$.2H$_2$O | 0.005 |
| H$_3$BO$_3$ | 0.01 |
| KCl | 0.02 |
| HCl (concentrated) | 2.0 ml/L |

The medium was prepared with distilled water, pH to 7.0 prior to sterilization. Glucose was autoclaved separately. It was dispensed in 500 ml bottles and autoclaved at 121° C. for 15 minutes.

Liquid Production Medium 1

| Component | g/L |
|---|---|
| Glycerol | 75.0 |
| Glucose | 75.0 |
| Tomato paste | 5.0 |
| NZ amine Type A | 4.0 |
| Ardamine PH | 5.0 |
| K$_2$HPO$_4$ | 0.5 |
| MgSO$_4$.7H$_2$O | 0.25 |

-continued

Liquid Production Medium 1

| Component | g/L |
|---|---|
| KCl | 0.25 |
| ZnSO$_4$.7H$_2$O | 0.5 |
| CaCO$_3$ | 10.0 |

The medium was prepared with distilled water, pH to 7.0 prior to sterilization. The medium was dispensed at 50 ml per 250 ml unbaffled Erlenmeyer flask. The flasks were closed with cotton and autoclaved at 121° C. for 20 minutes.

Solid Production Medium 2
1. Solid portion:
   Add 675 cc vermiculite to a 2-liter roller bottle. Plug with latex closure; autoclave for 60 min., plus 30 min. dry.
2. Liquid portion:
   To a 500 ml bottle, add 220 ml of the following:

| Component | g/L |
|---|---|
| Sucrose | 60.0 |
| Glucose | 80.0 |
| Glycerol | 60.0 |
| Citric Acid | 15.0 |
| NZ amine Type A | 5.0 |
| NaNO$_3$ | 1.0 |
| KH$_2$PO$_4$ | 0.5 |
| MgSO$_4$.7H$_2$O | 0.5 |
| CaCO$_3$ | 0.5 |
| K-elements | 1 ml/L |
| K-elements Component | |
| FeCl$_3$.6H$_2$O | 5.8 |
| MnSO$_4$.H$_2$O | 0.1 |
| CoCl$_2$.6H$_2$O | 0.02 |
| CuSO$_4$.5H$_2$O | 0.015 |
| Na$_2$MoO$_4$.2H$_2$O | 0.012 |
| ZnCl$_2$ | 0.02 |
| SnCl$_2$.2H$_2$O | 0.005 |
| H$_3$BO$_3$ | 0.01 |
| KCl | 0.02 |
| HCl (concentrated) | 2.0 ml/L |

The medium was prepared with distilled water, pH to 7.0 prior to sterilization. It was dispensed at 220 ml per 500 ml bottle and autoclaved at 121° C. for 15 minutes.

Liquid Production Medium 2

The composition is the same as the liquid portion of Solid Production Medium 1. The medium was prepared with distilled water, pH to 7.0 prior to sterilization. Glucose was autoclaved separately. The medium was dispensed at 50 ml per 250 ml unbaffled Erlenmeyer flask. The flasks were closed with cotton and autoclaved at 121° C. for 15 minutes.

EXAMPLE 1

Production of Sordarin by Fermentation of *Rosellina subiculata* (MF6239, ATCC 74386)

1. CULTURE: A portion of the agar slant containing the culture was aseptically transferred to seed medium 1 (50 ml/250 ml unbaffled flask). This was incubated on a 2-inch throw gyratory shaker, 220 rpm for 5 days at 25° C., 85% relative humidity (rh), to obtain biomass. Portions of the biomass were transferred into sterile vials containing glycerol and frozen (as frozen vegetative mycelia (FVM)). These were maintained in a final concentration of 10–15% glycerol at −75° C. Secondary FVMs were prepared from a primary FVM by transferring 1.0 ml of the thawed primary FVM into seed medium 2, incubating 7 days at 25° C., 220 rpm and freezing as above.

2. SEED: A frozen vial (FVM) of MF6239 was thawed to room temperature and used to inoculate seed cultures with 1.0 ml per 50 ml seed medium 2. These were grown on a gyratory shaker (220 rpm) for 7 days at 25° C., 85% rh.

3. PRODUCTION: On solid production medium. An aliquot (10–12 ml) of the seed was placed into 220 ml of the liquid portion of solid production medium 1. This flask was swirled vigorously to disperse the biomass. The contents were dispensed by pouring into a 2 L roller culture vessel which contained 675 cubic centimeters of large-particle vermiculite. The contents of the roller bottle were shaken/mixed to insure homogeneous inoculation and coverage. The roller bottles were incubated horizontally, revolving at approximately 4 rpm on a Wheaton roller apparatus, at 22° C., 70% rh for 17 days, to obtain a secondary metabolite in the fermentation medium.

In liquid production medium. Seed cultures were inoculated as described above. An aliquot of the seed (1.5 ml) was used to inoculate each production flask, containing 50 ml/250 ml flask of liquid production medium 1. Flasks were incubated on a gyratory shaker (220 rpm) for 7–21 days at 25° C., 50–85% rh.

EXAMPLE 2

Production of Sordarin by Fermentation of MF6232 (ATCC 74387)

1. CULTURE: A portion of the agar slant containing MF6232 was aseptically transferred to seed medium 1 (50 ml / 250 ml unbaffled flask). This was incubated on a 2-inch throw gyratory shaker, 220 rpm for 3 days at 25° C., 85% relative humidity (rh), to obtain biomass. Portions of the biomass were transferred into sterile vials containing glycerol and frozen (as FVM). These were maintained in a final concentration of 10–15% glycerol at −75° C. Secondary FVMs were prepared from a primary FVM by transferring 1.0 ml of the thawed primary FVM into seed medium 2 (composition below), incubating 7 days, 25° C., 220 rpm, and freezing as above.

2. SEED: A frozen vial (FVM) of MF6232 was thawed to room temperature and used to inoculate seed cultures with 1.0 ml per 50 ml seed medium 2. These were grown on a gyratory shaker (220 rpm) for 7 days at 25° C., 85% rh.

3. PRODUCTION: On solid production medium. An aliquot (10–12 ml) of the seed was placed into 220 ml of solid production medium 2. This was swirled vigorously to disperse the biomass. The contents were dispensed by pouring into a 2L roller culture vessel which contained 675 cubic centimeters of large-particle vermiculite. The contents of the roller bottle were shaken/mixed to insure homogeneous inoculation and coverage. The roller bottles were incubated horizontally, revolving at approximately 4 rpm on a Wheaton roller apparatus, at 22° C., 70% rh for 21 days, to obtain a secondary metabolite in the fermentation medium.

In liquid production medium. Seed cultures were inoculated as described above. An aliquot of the seed (1.5 ml) was used to inoculate each production flask, containing 50 ml/250 ml flask of liquid production medium 2. Flasks were incubated on a gyratory shaker (220 rpm) for 7–21 days at 25° C., 50–85% rh.

EXAMPLE 3

Large Scale Production of Sordarin by MF6232 (ATCC 74387)

The liquid portion of solid production medium 1 was used for both the seed and production fermenters. Cerelose, added post-sterilely, in the seed fermenter medium was 30 g/L while that of the production fermenter medium was 150 g/L. Seed fermenters were inoculated with 2 L of culture grown in shaker flasks. These fermenters were permitted to grow at 25° C. for 30 hours until the oxygen uptake rate was about 3 mmol/L-hr. At 30 hours, 25 L of fermenter seed culture was transferred to the production fermenter.

Growth in the production fermenter reached 8–10 mmol/L-hr after 50 hours and declined to between 5–7 by the end of the cultivation. Dissolved oxygen was controlled by increasing agitation. Broth pH was not controlled and generally decreased to 5.3 at 200 hours. The temperature was 25° C.

After 280 hours of growth the fermentation was terminated and the preparations for harvest begun. The pH was adjusted to about 12 with sodium hydroxide and the batch aged for 20 hours at fermentation temperature. The pH was then adjusted to 6.0 with sulfuric acid prior to transfer into drums for further processing.

EXAMPLE 4

Isolation of Sordarin

ISOLATION I

A methyl ethyl ketone extract of the fermentation of culture MF6232 (ATCC 74387) corresponding to 64 mL of whole broth was concentrated to dryness in vacuo (365 mg). This material was dissolved in 2 parts methanol in 98 parts methylene chloride to a final volume of 4.6 ml. A 4.3 ml portion (341 mg) was applied to a 60 ml silica gel 60 (0.040–0.0630 mm, 230–400 mesh, E. Merck) flash chromatography column equilibrated with 2 percent methanol in methylene chloride. The column was eluted by a step gradient of 240 ml each of 2, 5, 10, and 30 percent methanol in methylene chloride followed by 120 ml of methanol. Sixteen 15 ml fractions were collected from each solvent system. The product rich fractions 39–56 were determined by biological assay.

The crude fraction pool was concentrated to dryness in vacuo (103.1 mg). A 34.4 mg portion of this sample was further purified by HPLC separation (Zorbax Rx-C8, 5 $\mu$m, 9.4 mm×250 mm, eluted with mobile phase consisting of 20% acetonitrile/80% aqueous 0.01 M $K_2HPO_4$ adjusted to pH 6.9 with concentrated $H_3PO_4$, flow rate 4 ml/min. at 40° C., diode array detection). Four milliliter fractions were collected. The product rich fractions 16–20 were pooled and concentrated in vacuo to approximately twenty-five percent of the original volume. The concentrate was doubly extracted with an equal volume of ethyl acetate and the ethyl acetate layers were washed with an equal volume of brine, dried over anhydrous $Na_2SO_4$ and concentrated in vacuo to yield 3.7 mg of sordarin.

ISOLATION II

A methyl ethyl ketone extract of the batch −004Y fermentation of culture MF6232 ($ATCC_{74387}$) corresponding to 980 mL of whole broth was concentrated to dryness in vacuo (4.9 g). This material was dissolved in 1 part methanol in 9 parts methylene chloride to a final volume of 21.5 ml. A 21 ml portion (4.8 g) was applied to a 500 milliliter silica gel 60 (0.040–0.0630 mm, 230–400 mesh, E. Merck) chromatography column equilibrated with 2 percent methanol in methylene chloride. The column was eluted at a flowrate of 25 ml/min. by a step gradient beginning with 1 liter each of 2 and 5 percent methanol in methylene chloride followed by 2 liters of 15 percent methanol. The column elution was completed with 1 liter each of 30 and 100 percent methanol. Twenty-five milliliter fractions were collected. Product rich fractions 75–85 and 111–121 were determined by biological assay and contained Compound I by RP HPLC analysis under acidic conditions.

The crude fraction pools, 75–85 and 111–121 were concentrated, separately, to dryness in vacuo (69.3 mg and 95.3 mg, respectively). Two 34 mg portions of pool 75–85 were further purified by two identical HPLC separations (Zorbax Rx-C8, 7 μm, 21.2 mm×250 mm, eluted with mobile phase consisting of 40% acetonitrile/60% H$_2$O with 0.1% H$_3$PO$_4$ overall, flow rate 20 ml/min. at 25° C., 220 nm). Ten milliliter fractions were collected. The product rich fractions 27–31 from both runs were pooled together and concentrated in vacuo to approximately forty percent of the original volume. The concentrate was extracted with an equal volume of ethyl acetate and washed with an equal volume of brine, dried over anhydrous Na$_2$SO$_4$ and concentrated in vacuo to yield 27 mg of sordarin. Two 46 mg portions of pool 111–121 were also further purified under the identical HPLC conditions listed above. Fractions 25–28 from both runs were combined and prepared as described above to yield an additional 17 mg of sordarin.

EXAMPLE 5

Biological Evaluation of Sordarin

1. Action against *Erysiphe graminis* on wheat.

a) After 1 week cultivation, wheat plants are sprayed to run off with a spray mixture (200 ppm active ingredient/20% acetone/0.25% Triton X155). After 2 hours, the treated plants are infected with ascospores shaken from inoculum plants. Fungal attack is evaluated after incubation for 8 days at 22° C. at 50% relative humidity to determine the protection given by the compound.

b) After 1 weeks cultivation, wheat plants are infected with ascospores shaken from inoculum plants. After 24 hours, the wheat plants are sprayed with a spray mixture (200 ppm active ingredient/ 20% acetone/0.25% Triton X155). Fungal attack is evaluated after incubation for 8 days at 22° C. at 50% relative humidity to determine the degree of curative activity provided by the compound.

c) After 1 weeks cultivation, wheat plants are infected with ascospores shaken from inoculum plants. After 24 hours, the soil in which the wheat plants are growing is drenched with the drench mixture (200 ppm active ingredient/20% acetone/0.25% Triton X155). Fungal attack is evaluated after incubation for 8 days at 22° C. at 50% relative humidity to determine the degree of curative activity provided by the compound.

Wheat plants that had been treated with a mixture containing sordarin exhibited 100% control of fungal infection at 200 ppm in all three tests, that is, it demonstrated strong protectant, curative and systemic activity against *Erysiphe graminis* on wheat 2. Action against *Puccinia recondita* on wheat a) After 1 weeks cultivation, wheat plants sprayed to run off with a spray mixture (200 ppm active ingredient/20% acetone/0.25% Triton X155). After 2 hours, the treated plants are infected with a spore. Fungal attack is evaluated after incubation for 1 day at 95–100% relative humidity at 20° C. followed by 7 days at 25° C. at 50% relative humidity to determine the protection given by the compound.

b) After 1 weeks cultivation, wheat plants are infected with a spore suspension After 24 hours, the infected plants are sprayed to run off with a spray mixture (200 ppm active ingredient/20% acetone/0.25% Triton X155. Fungal attack is evaluated after incubation for 1 day at 95–100% relative humidity at 20° C. followed by 7 days at 25° C. at 50% relative humidity to determine the degree of curative activity provided by the compound.

c). After 1 weeks cultivation, wheat plants are infected with a spore suspension After 24 hours, the soil in which the wheat plants are growing was drenched with the drench mixture (200 ppm active ingredient/20% acetone/0.25% Triton X155). Fungal attack is evaluated after incubation for 1 day at 95–100% relative humidity at 20° C. followed by 7 days at 25° C. at 50% relative humidity to determine the degree of curative activity provided by the compound.

Wheat plants that had been treated with a mixture containing sordarin exhibited 100% control of fungal infection at 200 ppm in all three tests, that is, it demonstrated strong protectant, curative and systemic activity against *Puccinia recondita* on wheat

What is claimed is:

1. A biologically pure culture of *Rosellinia subiculata* strain ATCC 74386.

2. A biologically pure culture of a fungus strain ATCC 74387.

3. An agricultural composition comprising a sordarin compound and an agriculturally acceptable carrier thereof, wherein said sordarin compound is produced by a microorganism strain selected from the group consisting of *Rosellinia subiculata* strain ATCC 74386 and fungus strain ATCC 74387.

4. A method for the production of a sordarin compound which comprises:

cultivating a biologically pure culture of *Rosellinia subiculata* strain ATCC 74386 in a nutrient medium containing assimilable sources of carbon and nitrogen; and recovering said sordarin compound from said medium.

5. A method for the production of a sordarin compound which comprises:

cultivating a biologically pure culture of fungus strain ATCC 74387 in a nutrient medium containing assimilable sources of carbon and nitrogen; and recovering said sordarin compound from said medium.

6. A method for controlling phytopathogenic fungi which comprises administering to a plant in need of such treatment an antifungal effective amount of a sordarin, compound produced by a microorganism strain selected from the group consisting of *Rosellinia subiculata* strain ATCC 74386 and fungus strain ATCC 74387 wherein said phytopathogenic fungi is selected from the group consisting of: *Erysiphe graminis, Puccinia recondita, Stagnospora nodorum, Septoria tritici, Pyricularia oryzae, Phytophthora infestans, Plasmopara viticola* and *Botrytis cinerea*.

* * * * *